United States Patent [19]

Walton, II

[11] 4,441,563

[45] Apr. 10, 1984

[54] TOOL COLLET AND CONTROL MEANS

[75] Inventor: Richard E. Walton, II, Fallston, Md.

[73] Assignee: Black & Decker Inc., Newark, Del.

[21] Appl. No.: 317,151

[22] Filed: Nov. 2, 1981

[51] Int. Cl.³ .............................................. A61B 17/18
[52] U.S. Cl. ..................................... 173/163; 173/167; 128/92 EC
[58] Field of Search .......................... 173/163, 167, 46; 279/30, 51, 75; 128/92 EB, 92 EC, 303, 305

[56] References Cited

U.S. PATENT DOCUMENTS

| 2,735,687 | 2/1956 | Cox | 279/51 |
| 3,712,386 | 1/1973 | Peters | 173/46 |
| 3,718,340 | 2/1973 | Stewart | 279/57 |
| 3,724,563 | 4/1973 | Wickham et al. | 173/163 |
| 4,109,735 | 8/1978 | Bent | 173/163 |
| 4,346,765 | 8/1982 | Workman, Jr. | 173/12 |

Primary Examiner—E. R. Kazenske
Assistant Examiner—W. Fridie, Jr.
Attorney, Agent, or Firm—R. B. Sherer; Harold Weinstein; Charles E. Yocum

[57] ABSTRACT

A power tool, such as a surgical drill, has a tool element retained in a collet coupled to the output spindle of the tool. Resilient member constantly maintains the collet in its closed position. Upon rotation of the spindle in a reverse direction, opposite to its normal driving direction, a cam is actuated to open the collet against the force of the resilient member, thereby facilitating removal of the tool element from the collet. Preferably, the tool is of the cordless type and has a reversible electric motor controlled by a pair of triggers mounted on the pistol-grip handle for the tool. The triggers are conveniently disposed adjacent to each other and are easily distinguishable from one another, thereby providing for a convenient one-hand operation of the tool.

27 Claims, 19 Drawing Figures

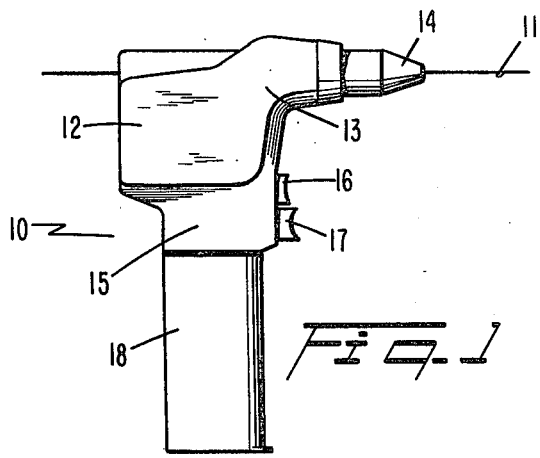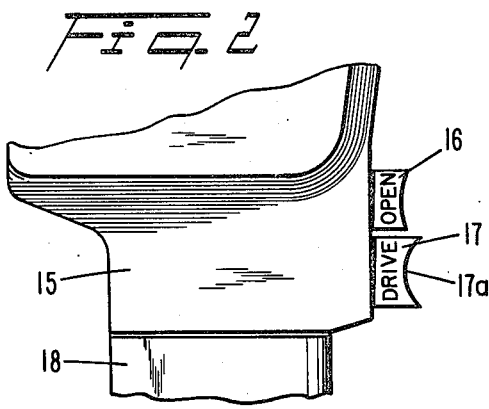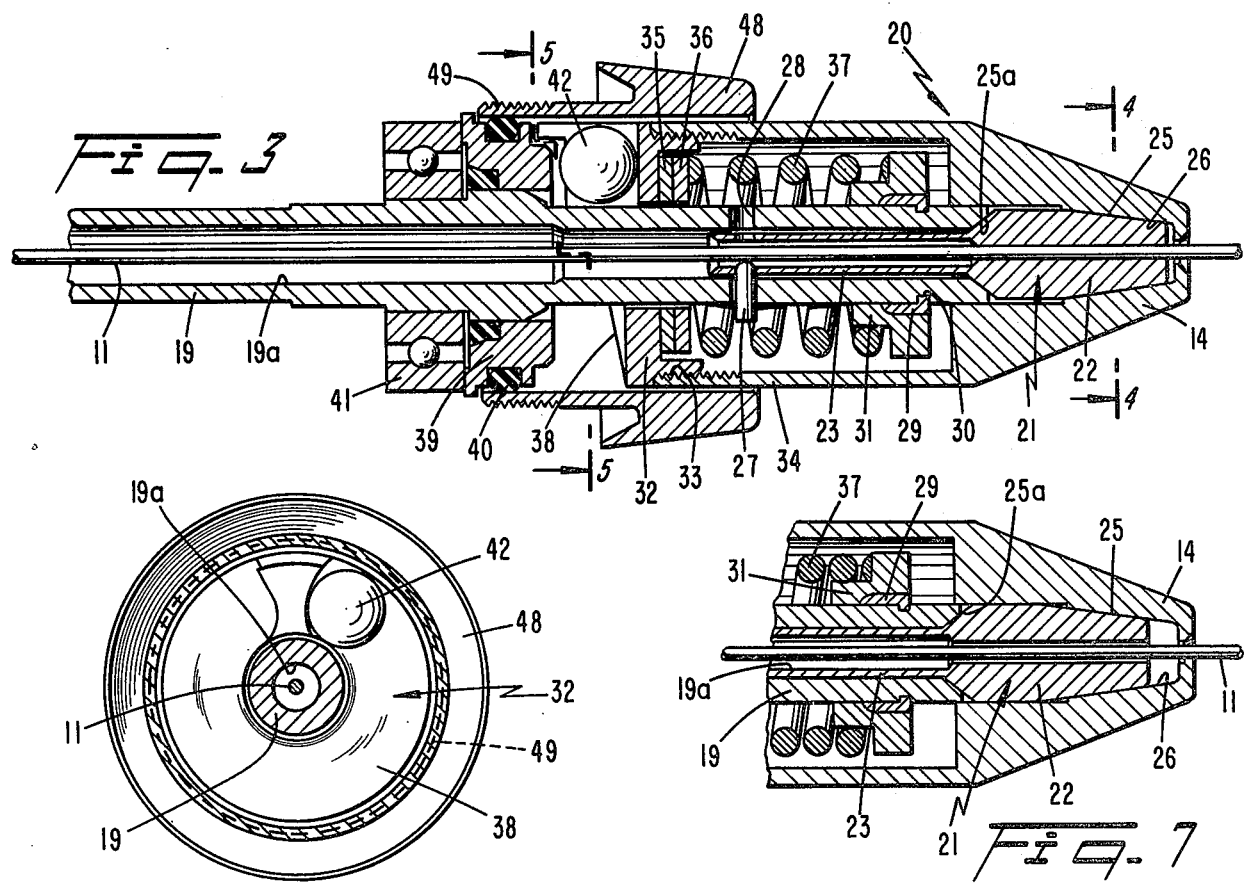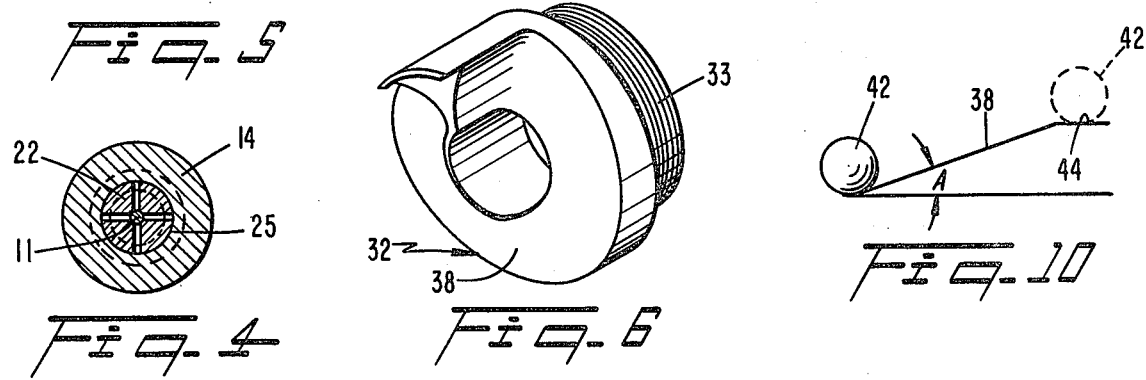

STEP ONE

DEPRESS "OPEN" AND INSERT K-WIRE
(TO DESIRED LENGTH BEYOND UNIT)

STEP TWO

DEPRESS "DRIVE" AND RELEASE

NOTE

K-WIRE IS RETAINED, EVEN
THOUGH UNIT IS INVERTED.

STEP THREE

DEPRESS "DRIVE" AND ADVANCE
K-WIRE INTO PATIENT

STEP FOUR

DEPRESS "OPEN" AND RETRACT UNIT
(K-WIRE IS ANCHORED IN PATIENT)

- CYCLE MAY BE REPEATED -

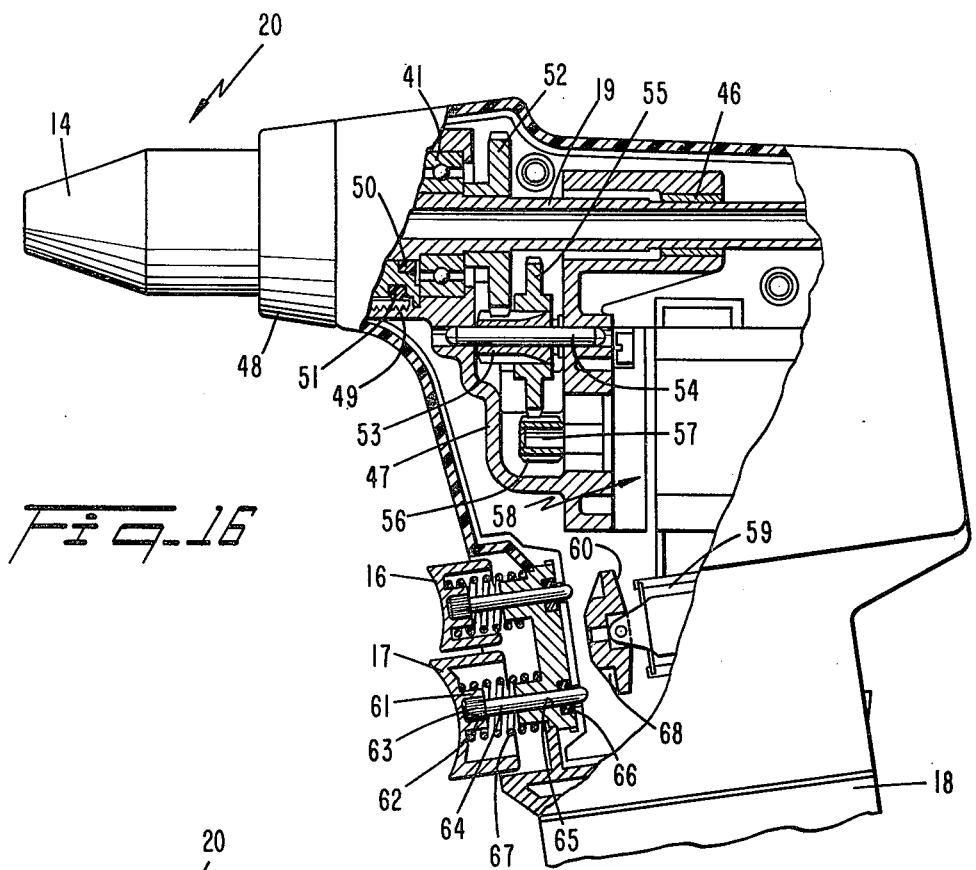
Fig_16
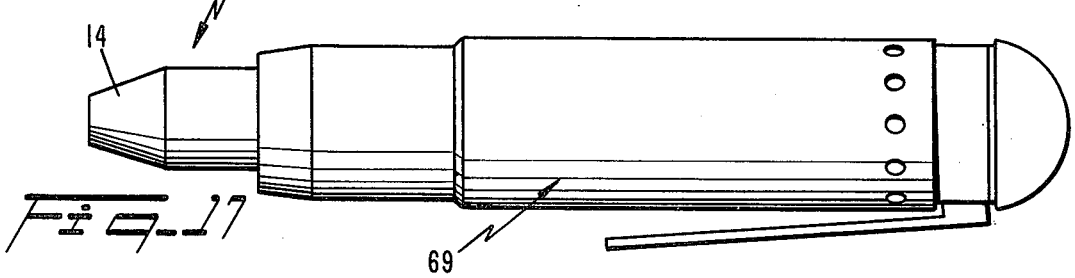
Fig_17
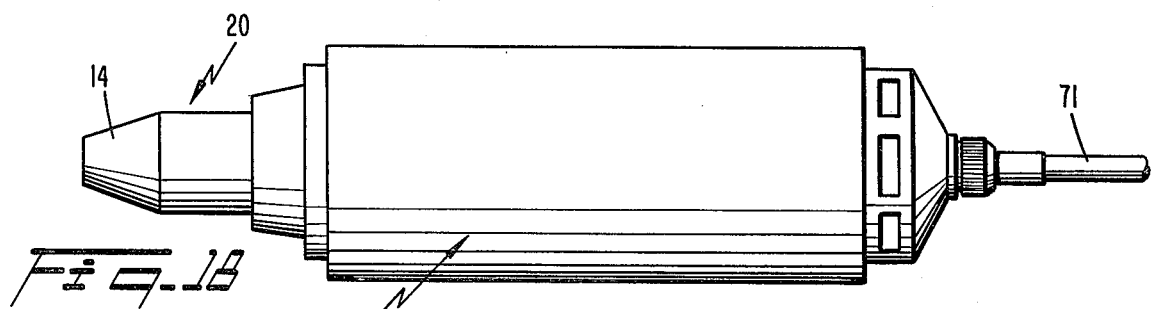
Fig_18
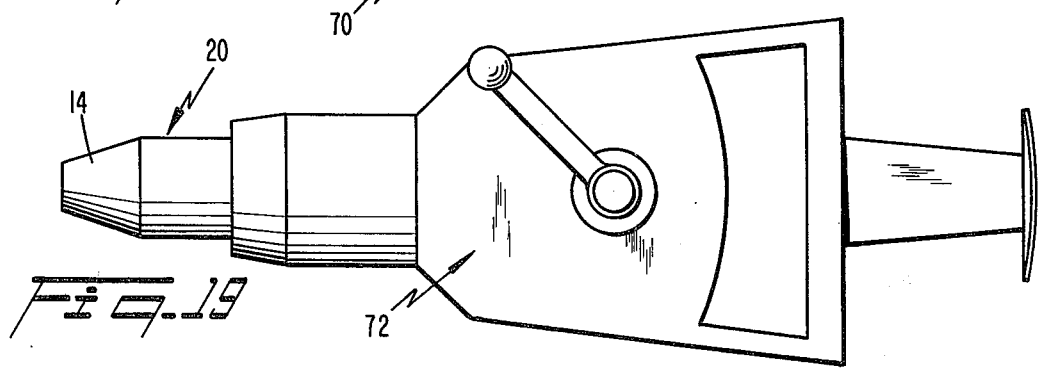
Fig_19

TOOL COLLET AND CONTROL MEANS

BACKGROUND OF THE INVENTION

In the prior art, of which I am aware, portable electric drills and other power tools traditionally employ a chuck or collet to securely retain the drill bit or other tool element therein and facilitate its advancement into the workpiece. In portable electric drills intended for consumer usage, a geared chuck and conventional chuck key are employed. For drills intended for heavy-duty industrial applications, the chuck may be of the conventional geared type or else of the keyless type. In both cases, the chucks are operated manually.

Manually-operated chucks and collets have also been used to hold various tools and workpieces in the machine arts. One example is the cam-operated chuck disclosed in U.S. Pat. No. 2,735,687. In that patent, a plurality of balls cooperate with a cam formed on the collet, and the collet opens or closes in response to the direction in which a hand wheel is turned.

Besides the manually-operated chucks, the prior art has also resorted to air-operated chucks for lathes and other machine tools. This general concept has also been applied to a portable pneumatic tool as disclosed in U.S. Pat. No. 3,712,386. In that patent, the pressure of the compressed air selectively operates a reciprocatory spring-loaded piston to open the gripping jaws of the tool collet, thereby providing a quick-release feature. Alternately, as disclosed in U.S. Pat. No. 3,724,563, the pivoted lever for throttle control of a portable pneumatic tool is moved in a direction opposite to its normal mode of operation to actuate a mechanical linkage to open the tool collet.

In drills used for surgical or orthopedic purposes, a cannulated spindle has a through bore for receiving a Kirchner pin, usually referred to in the art as a "K wire". The K-wire is retained in a collet or chuck mounted on the forward end of the spindle. In some commercial embodiments, a pivoted release lever facilitates insertion of the K-wire (and its subsequent advancement relative to the drill) without the use of additional keys and accessories. The lever has a bifurcated portion engaging a spring-loaded slidable collar that actuates a mechanism to open the chuck. The remaining portion of the lever is bent around the trigger, forwardly thereof and providing a guard therefor, and terminates in a depending portion. One finger on the doctor's hand engages the trigger, while the doctor's remaining fingers are wrapped around the depending portion of the lever during operation of the tool. This is somewhat awkward and inconvenient. Moreover, in order to preclude inadvertent release of the collet during a surgical procedure, the spring pressure must of necessity be relatively heavy. As a result, whenever release of the collet is desired, a strong force must be exerted on the lever by the doctor. Repeated opening and closing of the collet can thus be tiresome during an extended surgical procedure.

In another commercial embodiment, a surgical tool is equipped with a pneumatic collet controlled by a trigger projecting forwardly of the pistol-grip handle of the tool. When the trigger is depressed partially, the collet closes; to securely retain the K-wire therein; and when the trigger is depressed fully, the tool is energized to drive the wire. While facilitating insertion and removal of the K-wire from the collet, the operator must continually depress the trigger by a predetermined amount to maintain the collet closed and to preclude inadvertent release of the K-wire. This detracts from the doctor's concentration and interferes with close surgical procedures in an operating room or clinic. Moreover, if the trigger would be completely released and the tool subsequently tilted or inverted, the K-wire could fall out of the tool and would no longer be usable because of hygienic considerations.

A possible solution is the surgical drill disclosed in U.S. Pat. No. 3,718,340. In that patent, a pivoted lever is mounted on the side of the drill. Actuation of the lever initiates a mechanical linkage to ultimately open the gripping jaws of the collet to release the K-wire. However, not only does actuation of the lever require a partial release of the doctor's hand grip, but of necessity, the drill is oriented for "right handed" usage. Moreover, a heavy spring pressure is required to maintain the collet in its closed position and preclude inadvertent release of the K-wire. To overcome this heavy spring pressure, the lever actuates the collet through a mechanical linkage. This mechanical linkage includes a pivoted yoke, a spring-loaded slide, a plurality of cam levers, respective push rods, and a hollow cone to actuate the gripping jaws of the collet. This linkage is unduly complicated, hence expensive and potentially unreliable.

Thus, the collets and chucks for surgical drills and other power tools, resorted to in the prior art, have had certain inherent disadvantages or deficiencies; and despite the highly-deveLoped state of the art, a practical, economical and reliable solution to a problem of long standing has heretofore eluded the designers and researchers in the field.

SUMMARY OF THE INVENTION

Accordingly, it is an object of the present invention to provide a quick-release collet for a power tool that alleviates the disadvantages and deficiencies of the prior art.

It is another object of the present invention to provide for use in a power tool, such as a surgical drill, a quick-release collet means which is simple and reliable in its operation, economical to produce, and convenient to use.

It is yet another object of the present invention to provide a collet means which closes in the forward direction of spindle rotation corresponding to the drilling mode of operation of the tool, remains closed as long as the spindle rotates (or is poised to rotate) in its forward direction, and opens upon reverse rotation of the spindle.

It is yet still another object of the present invention to provide a collet that is biased to a closed position and remains closed as the spindle rotates (or is poised to rotate) in its forward direction, and wherein a cam-actuated mechanism overcomes the resilient means to open the collet upon driving the spindle in its reverse direction.

It is a further object of the present invention to provide a cam means for opening the collet in response to reverse rotation of the spindle, wherein the cam means functions as an overrunning clutch during forward rotation of the spindle and as a slip clutch during reverse rotation.

It is a still further object of the present invention to provide a cam means having a cam track whose helix angle is less than 7 degrees.

It is a yet still further object of the present invention to provide a ball engaging the cam track, wherein the cam track terminates on its high side in a flat ledge for positioning the ball thereon upon reverse rotation of the spindle to open the collet.

It is again an object of the present invention to provide a surgical drill having a cannulated spindle for receiving a K-wire, wherein the K-wire is received within a collet that is opened upon engagement of an "open" trigger and conversely, is closed upon engagement of a "drive" trigger, the triggers being mounted forwardly of the pistol-grip handle for the tool.

It is again another object of the present invention to provide a cordless surgical drill having a reversible electric motor, wherein engagement of the "open" trigger reverses the direction of rotation of the motor and opens the collet to release the K-wire, wherein engagement of the "drive" trigger energizes the motor in its normal direction of rotation and closes the collet to retain the K-wire therein, and wherein the K-wire is retained within the drill even though the "drive" trigger is not depressed continuously.

It is again a further object of the present invention to provide a pair of triggers on the pistol-grip handle of a surgical drill, the triggers being disposed adjacent to each other, and the triggers being human engineered for immediate distinction from each other, thereby facilitating a convenient one-hand operation of the surgical drill without requiring the doctor to look at the triggers, and without requiring a repositioning or loosening of the doctor's hand on the pistol-grip handle.

In accordance with the broad teachings of the present invention, a tool has a housing with a spindle journaled therein for rotation in forward and reverse directions, respectively. A collet means is provided for retaining a tool element driven by the spindle. The collet has an open position and a closed position, respectively. Frictional means constantly urges the collet means in its closed position, and the collet means remains closed in the forward direction of rotation of the spindle corresponding to the driving mode of operation of the tool. A cam means is provided, responsive to rotation of the spindle in the reverse direction, to move the collet means from its closed position into its open position against the force of the frictional means.

One embodiment of the teachings of the present invention comprises a surgical drill having a cannulated driving spindle provided with a longitudinal through bore for receiving a K-wire or the like. A nose housing encloses the spindle and has an internally-tapered forward portion and a cylindrical rearward portion. A slotted collet is driven by the spindle and has an externally-tapered portion projecting forwardly of the spindle and seated within the complementary internally-tapered forward portion of the nose housing. The collet has an open position and a closed position. A shoulder member is mounted on the spindle; and a cam is freely mounted on the spindle rearwardly of the shoulder member, and is secured to the rearward cylindrical portion of the nose housing. A stationary thrust ring is retained in the housing rearwardly of the cam. The rearward portion of the cam is formed with a cam track, and a ball (or equivalent cam follower) is disposed between the cam track and the thrust ring. A compression spring (or other suitable resilient means) is disposed between the cam and the shoulder member, constantly urging the cam and hence the nose housing in a direction rearwardly of the spindle, and thereby closing the collet and securing the K-wire therein. The ball has a loose engagement in the cam track in one direction of rotation of the spindle, corresponding to the drive position of the tool. However, in the opposite direction of spindle rotation, (obtained by reversal of the motor) the cam track engages the ball to move the cam and hence the nose housing axially along the spindle and forwardly of the drill, and against the force of the spring, thereby separating the complementary tapered portions of the collet and nose housing, respectively, and thereby opening the collet to facilitate release of the K-wire therefrom.

These and other objects of the present invention will become apparent from a reading of the following specification, taken in conjunction with the enclosed drawings.

BRIEF DESCRIPTION OF THE DRAWINGS

FIG. 1 is a side elevation of a surgical drill, wherein a preferred embodiment of the present invention may find particular utility;

FIG. 2 is an enlarged fragmentary portion of FIG. 1, showing the "open" trigger for releasing the collet, and further showing the "drive" trigger for closing the collet and energizing the tool;

FIG. 3 is a partial longitudinal section view of the forward portion of the drill of FIG. 1, drawn to an enlarged scale, and showing a preferred embodiment of the collet means of the present invention, the collet means being shown in its closed position;

FIG. 4 is a section view, taken along the lines 4—4 of FIG. 3, showing the K-wire retained in a slotted collet member of the collet means;

FIG. 5 is a stepped section view, taken along the lines 5—5 of FIG. 3, showing (in plan view) the cam track formed in the rearward portion of the cam;

FIG. 6 is a rear perspective view of the cam;

FIG. 7 is a longitudinal section, corresponding to a portion of FIG. 3, but showing the cam and nose housing moved forwardly of the spindle, thereby allowing the collet to move into its open position;

FIG. 10 is a plan layout of the cam track, the ball being shown (in broken lines) in a position corresponding to the open portion of the collet;

FIG. 16 is an enlarged elevation of the preferred embodiment, with parts broken away and sectioned; and FIGS. 17–19 are side elevations of additional tools in which the teachings of the present invention may be applied.

DESCRIPTION OF THE PREFERRED EMBODIMENT

Figure 8:
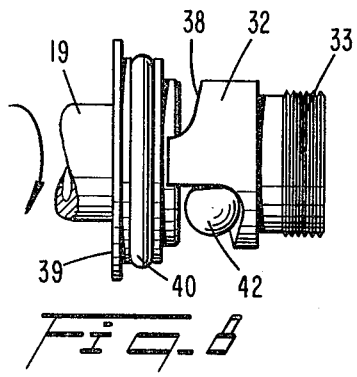
FIG. 8 is a view showing the thrust ring, ball and cam in elevation, the view corresponding to the closed position of the collet.

With reference to FIGS. 1 and 2, there is illustrated a surgical drill 10 with which the teachings of the present invention may find particular utility. It will be understood by those skilled in the art, however, that the surgical drill 10 constitutes only one embodiment of the present invention, and that the teachings of the present invention are equally applicable to a wide variety of tools and devices. With this in mind, the drill 10 is adapted to drive a Kirschner pin 11 (referred to in the art as a "K-wire") and comprises a motor housing 12, a gear housing 13 forwardly thereof, a nose housing 14 through which the K-wire projects, a depending pistol-grip handle 15, and a pair of triggers projecting forwardly of the pistol-grip handle, one comprising an "open" trigger 16 for opening the collet means and facilitating release of the K-wire, and other comprising a "drive" trigger 17 for closing the collet means and securing the K-wire therein, as hereinafter described in detail. Preferably the drill is cordless and has a removable battery pack 18 constituting part of the pistol-grip handle.

With reference to FIGS. 3 through 6, a driving output spindle 19 is journaled in bearings in the housing (as hereinafter described). The spindle is cannulated and has a longitudinal through bore 19a for receiving the K-wire 11. The K-wire is retained with respect to the spindle by the collet means 20 of the present invention. This collet means comprises a collet member 21 having a forward portion 22 and a rearward portion 23. The forward portion has a plurality of slots 24 (as shown more clearly in FIG. 4) and further has an annular externally-tapered portion 25 seated within a complementary internally tapered annular portion 26 of the nose housing. Preferably, the collet also has a reverse annular tapered surface 25a seated against a complementary annular tapered surface 19b on the spindle, thereby further maintaining concentricities. The rearward portion of the collet member is cylindrical and is received within the bore in the spindle. Preferably, but not necessarily, the collet is coupled to the spindle by means of a transverse pin 27 received (with axial clearance) within a transverse hole 28 in the spindle. A split keying ring 29 has an inwardly-extending annular portion received within an external annular groove 30 formed on the spindle. A stepped shoulder member 31 is slidably fitted over the spindle and is held against the split keying ring.

A cam 32 is freely mounted concentrically about the spindle and has a threaded connection 33 with the rearward cylindrical portion 34 of the nose housing. The cam and nose housing thereby form an integral subassembly and are free to move axially with respect to the spindle. Preferably, but not necessarily, a pair of thrust washers 35 and 36 are positioned forwardly of the cam. A compression spring 37 (or other suitable resilient means) is positioned concentrically about the spindle and is seated between the washers and the stepped shoulder member. The spring constantly urges the cam and hence the nose housing rearwardly of the spindle, thereby firmly seating the slotted tapered forward portion of the collet member within the internally-tapered forward portion of the nose housing, and thereby maintaining the collet in a closed position and securely retaining the K-wire therein.

A cam track 38 is formed on the rearward portion of the cam, and a stationary thrust ring 39 is retained within the housing. The thrust ring has a radial clearance with respect to the rotating spindle and is held in its stationary position by the frictional force exerted by an O-ring 40 which maintains the ring next to the inner race of the ball bearing 41. A cam follower is disposed between the thrust ring and the cam track formed on the cam. Preferably, the cam follower comprises a ball 42 (or other suitable anti-friction element) whose thrust surface is provided by the thrust ring.

Figure 9:
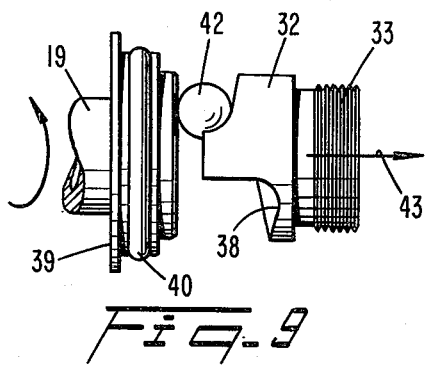
FIG. 9 corresponds to FIG. 8, but showing the cam track engaging the ball to move the cam forwardly of the spindle, the view corresponding to the open position of the collet.

With reference again to FIGS. 3 through 6, and with further reference to FIGS. 7 through 9, as long as the spindle 19 is rotating (or is positioned to rotate) in the direction of the arrow in FIG. 8, that is, clockwise as viewed from the rear of the spindle and looking forwardly of the drill, the collet 21 will remain in its closed position to securely retain the K-wire therein. In this position, the ball 42 has an axial clearance with respect to the cam 32 and thrust ring 39 (as shown in FIGS. 3 and 8) and for all intents and purposes, is inoperative relative to the cam track 38. However, when the direction of rotation of the spindle 19 is reversed, as indicated by the arrow in FIG. 9, (that is, counterclockwise as viewed from the rear of the spindle and looking forwardly of the drill) the cam track 38 engages the ball 42 and rides around the ball, as the ball moves relatively up the track, thereby moving the cam forwardly and axially along the spindle (as indicated by the large arrow 43 in FIG. 9). This cam action is against the frictional bias forces provided by the spring 37. Since the nose housing 14 is secured to the cam, the nose housing also moves forwardly, thereby separating the tapered portions 25 and 26 on the collet member and nose housing, respectively, and thereby opening the slotted collet member 21 to facilitate the withdrawal of the K-wire 11 therefrom. Nor must power always be used to open the collet. If desired, the collet may be opened manually by simply turning the nose housing, counterclockwise, about one-and-a-half turns.

Although the cam 32 is freely mounted relative to the spindle, there is inherent friction in the system created by the spring 37. This friction operates through the collet and nose housing to rotate the cam upon reverse rotation of the spindle. The ramp of the cam track 38 is on the moving surface (the cam 32) and acts as a wedge to engage the ball 42 which, being stationary, has inertia. The cam track moves around the ball to move the cam forwardly. If the cam were not formed on the surface of the moving member, the mechanism might not engage the cam follower and might possibly malfunction. With the disclosed structure, however, the cam always functions to open the collet, regardless of the position or orientation of the tool.

With reference to FIG. 10, the cam track has a ramp or helix angle A which is preferably less than 7 degrees. This assures that the relative movement between the ball and the cam track will be substantially smooth and uniform, and that the ball will not "shoot out" in its relative movement with respect to the rotating cam track. Moreover, the high point of the cam track terminates in a flat ledge 44 that serves to "park" the ball and preclude its relative movement back down the cam track.

Thus, it will be appreciated by those skilled in the art that the cam means functions on an overrunning clutch in the forward rotation of the spindle; and in the reverse direction, the cam means functions as a slip clutch, thereby precluding damage to the motor or undue drainage of the battery pack in the event the "open" trigger is not released and the motor is thus continually operated in the reverse direction.

Figure 11:
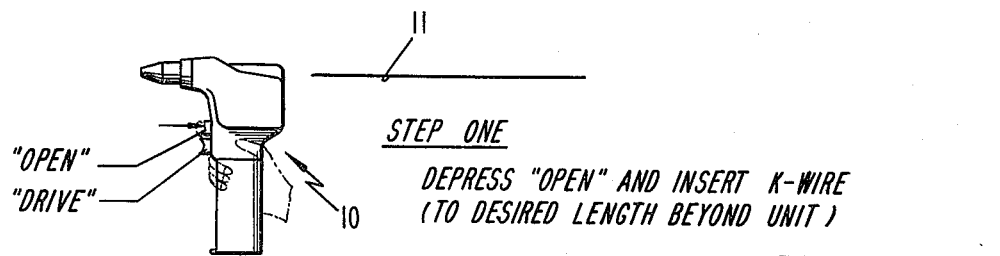
FIGS. 11–15 are schematic sequence views, showing the advantages in using the preferred embodiment of the present invention.
Figure 12:
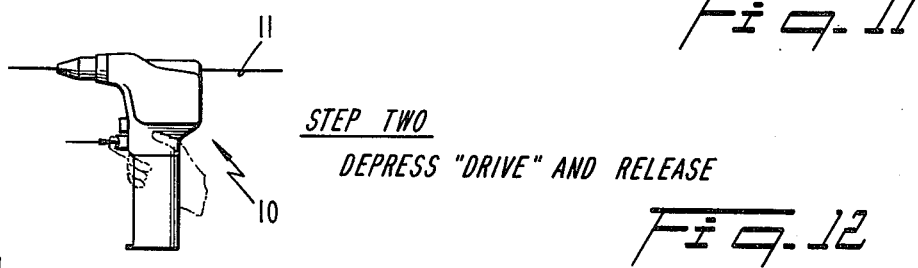
Figure 13:
Figure 14:
Figure 15:

With reference to FIGS. 11 through 15, the special advantages of the present invention (as applied to the surgical drill 10) will be appreciated. In FIG. 11, the "open" trigger 16 has been depressed to move the collet to its open position and facilitate insertion of the K-wire 11 into the drill. The drill is so designed as to enable the K-wire to be inserted from either the front or the back of the drill. The K-wire is manually advanced forwardly of the drill (to the desired amount) and the "drive" trigger is depressed to close the collet and hold the K-wire securely within the drill, as shown in FIG. 12. Thereafter, the K-wire will be held securely within the drill, even through the "drive" trigger is released. It is not necessary to continually depress the "drive" trigger, and the K-wire is retained until the "open" trigger is again depressed. This is an important feature of the present invention. Thus, as illustrated in FIG. 13, the doctor's (or operator's) hand need not be held on the drill, and indeed the drill can be inverted or tilted, without fear of having the K-wire fall out of the unit. This is especially important in surgical procedures in operating rooms, or orthopedic procedures in clinics, where hygienic cleanliness is mandatory. Thereafter, as shown in FIG. 14, the "drive" trigger is again depressed, driving the K-wire and advancing it into the bone 45 of the patient. To retract the drill rearwardly of the K-wire (to facilitate subsequent advance of the K-wire into the bone) the "open" trigger is depressed to open the collet. A portion of the K-wire is retained in the bone, and the drill is slidably moved along the K-wire to expose the desired additional length of K-wire to be inserted into the patient's bone. Thereafter, the "drive" trigger is again depressed and the cycle is repeated. When the desired length of K-wire has been fully positioned in the bone, the excess may be snipped off by suitable means.

During the surgical or orthopedic procedure (illustrated schematically in FIGS. 11–15) the doctor's hand may be held in the same position. This position need not be loosened or relocated relative to the pistol grip handle, nor is the doctor required to look at the triggers. The "open" and "drive" triggers, which are disposed adjacent to each other, are human engineered and readily distinguishable from one another. More specifically, the "drive" trigger 17 is larger than the "open" trigger 16 and has a forward face provided with an arcuate recess 17a formed therein (as shown in FIG. 2). Thus, the doctor may readily acquire a steady comfortable grip for immediate one-hand control without being distracted away from the delicate operation or procedure being performed. This is a salient advantage of the present invention over the prior art. Moreover, the drill may be used for either left-handed or right-handed operation.

Preferably, the drill is lightweight and powerful and is of the cordless type, thus eliminating the necessity for cords or hoses to power the drill. Thus, as shown in FIG. 16, the cannulated spindle is journaled fore and aft in the ball bearing 41 (previously noted) and a sleeve bearing 46, respectively. These bearings are suitably retained within a frame 47. Preferably, the motor housing and gear housing are formed as "clamshell" plastic members joined together along a common longitudinal midplane (not shown) and suitably secured to the frame. A ring 48 is threaded into the frame, as at 49, and retains the ball radially. Preferably, the ring carries sealing members 50 and 51. A gear 52 is press-fitted on the spindle and meshes with an intermediate gear 53 mounted on a stub shaft 54 retained within the frame. The gear 53 is formed as a cluster with a gear 55 which engages the pinion 56 of the armature shaft 57 of the motor 58. The motor is suitably mounted on the frame and is preferably of the high-efficiency permanent magnet type. The motor is reversible and is driven by the replaceable battery pack 18. The electrical connections between the motor and battery are omitted herewith for ease of illustration. The construction of the battery pack, motor and gearing (and their cooperation with each other) form no part of the present invention, but are shown herein to complete the disclosure.

With further reference to FIG. 16, the motor is controlled by a reversing switch 59 having a pivoted toggle memter 60. This toggle member is selectively engaged by the triggers 16 and 17, respectively. Each of the triggers is provided with a substantially identical mechanism to cooperate with the switch toggle; hence the mechanism will be described with reference only to "drive" trigger 17. Each trigger has a central boss 61 formed with a blind axial bore 62 for receiving the knurled portion 63 of a steel pin 64; preferably the trigger is molded integrally to the pin. The pin is slidably received within a bore 65 formed in the housing, and a seal 66 may be carried on the pin. A compression spring 67 is seated between the housing and the trigger and constantly urges the trigger forwardly of the housing. When the trigger is slidably depressed or retracted within the housing, the pin engages a pocket 68 on the pivoted switch toggle, thereby closing the switch and energizing the motor (which is reversible). The "drive" trigger 17 energizes the motor in its forward direction, and the "open" trigger 16 energizes the motor in its reverse direction (as previously noted). The surgical drill is completely sealed and may be suitably sterilized; however, the sealing means forms no part of the present invention, nor should the invention be limited thereby.

Indeed, as previously noted, the teachings of the present invention are broader than the surgical drill disclosed herein and are applicable to a wide variety of tools and devices. Examples are the portable pneumatic tool 69 of FIG. 17; the portable hobbyist tool 70 of FIG. 18, powered by a flexible cable 71; and the hand-operated drill 72 shown in FIG. 19. Each of these products has a spindle capable of forward and reverse operation.

Obviously, many modifications may be made without departing from the basic spirit of the present invention. Accordingly, it will be appreciated by those skilled in the art that within the scope of the appended claims, the invention may be practiced other than has been specifically described herein.

I claim:

1. In a tool having a housing with a spindle drivingly connected to a motor and journaled in the housing for rotation in a forward and reverse direction, respectively, the tool further having collet means for retaining a tool element driven by the spindle, and the collet means having an open position and a closed position, respectively, the improvement which comprises, in combination, frictional means for constantly urging the collet means in its closed position, the collet means remaining closed in the forward direction of rotation of the spindle corresponding to the driving mode of operation of the tool, and cam means, responsive to the motor rotating the spindle in the reverse direction, for moving the collet means from its closed position into its open position against the force of the frictional means, the cam means including a cam track and an antifriction cam follower operatively associated with the cam track, the antifriction cam follower being out of operative engagement with the cam track in the forward direction of rotation, and operatively engaging the cam track in the reverse direction of rotation, the cam means thereby being an overrunning clutch in the forward direction and a slip clutch in the reverse direction of rotation of the spindle.

2. In a portable tool having a housing with a driving spindle journaled therein for rotation in a forward and reverse direction, respectively, the tool further having collet means having an open and a closed position for retaining a driven tool element therein, the improvement which comprises, in combination, means including a resilient member for constantly urging the collet means in its closed position, the collet means remaining closed in the forward direction of rotation of the spindle corresponding to the driving mode of operation of the tool, and cam means responsive to reverse rotation of the spindle to move the collet means from its closed position into its open position against the bias force of the resilient member, thereby facilitating removal of the tool element from the collet means, the cam means functioning as an overrunning clutch in the forward direction, and the cam means including a cam member movable axially relative to the spindle, a stationary thrust ring in the housing, a cam track formed on the cam member, a ball loosely disposed axially between the thrust ring and the cam track in the forward direction of spindle rotation corresponding to the closed position of the collet means, and wherein the cam track engages the ball in the reverse direction of spindle rotation, thereby moving the cam member forwardly in the open position of the collet means.

3. The improvement of claim 2, wherein a shoulder member is carried by the spindle forwardly of the cam member, and wherein the resilient means comprises a compression spring disposed concentrically about the spindle and seated axially between the cam member and the shoulder member.

4. The combination of claim 2, further including a nose housing concentrically about the collet means.

5. In a portable tool having a housing with a driving spindle journaled therein for rotation in a forward and reverse direction, respectively, the tool further having collet means having an open and a closed position for retaining a driven tool element therein, the improvement which comprises, in combination, means including a resilient member for constantly urging the collet means in its closed position, the collet means remaining closed in the forward direction of rotation of the spindle corresponding to the driving mode of operation of the tool, a nose housing located concentrically about the collet means, the collet means including a collet member having a rearward portion and a radially-enlarged slotted forward portion to receive the tool element, the forward portion projecting forwardly of the spindle and being seated between the spindle and the nose housing, and cam means responsive to reverse rotation of the spindle to move the collet means from its closed position into its open position against the bias force of the resilient member, thereby facilitating removal of the tool element from the collet means, the cam means functioning as an overrunning clutch in the forward direction.

6. The improvement of claim 5, wherein the collet member has a rearward portion received within the bore of the spindle.

7. The improvement of claim 14, wherein the rearward portion of the collet member is secured to the spindle for rotation in unison.

8. The combination of claim 5, further including complementary tapers formed on the nose housing and the forward portion of the collet member, respectively, and on the spindle and the collet member, respectively.

9. The improvement of claim 5, wherein the nose housing has a rearward portion secured to the cam member, whereby the spring constantly urges the cam and hence the nose housing rearwardly of the spindle, thereby holding the nose housing firmly against the collet member to maintain the collet member in its closed position.

10. In a tool, the combination of a spindle journaled for rotation in the tool, the spindle having forward and reverse directions of rotation, respectively, a slotted collet mounted forwardly of the spindle, the collet having an open position and a closed position for retaining a driven tool element therein, a nose housing concentrically around the collet and spindle, the nose housing having a forward portion and a cylindrical rearward portion, the forward portion having a tapered internal annular surface, the collet having a complementary tapered external annular surface for seating the collet within the nose housing, a cam secured to the rearward portion of the nose housing, the cam and nose housing being free to move axially of the spindle, a shoulder on the spindle, a compression spring disposed concentrically about the spindle and seated axially between the cam and the shoulder, thereby constantly urging the cam and nose housing rearwardly of the spindle, and thereby firmly seating the collet within the nose housing to maintain the collet in its closed position during forward rotation of the spindle, a stationary thrust ring in the tool concentrically of the spindle and rearwardly of the cam, the cam having a cam track formed therein, and a cam follower between the cam and the thrust ring, whereby upon reverse rotation of the spindle, the cam track engages the cam follower to move the cam and nose housing forwardly of the spindle, thereby separating the nose housing from the collet, and thereby opening the collet to facilitate removal of the tool element therefrom.

11. The combination of claim 10, wherein the cam follower is out of engagement with the cam track in the forward direction of rotation of the spindle, corresponding to the normal driving mode of operation of the tool, whereby the cam functions as an overrunning clutch during operation of the tool.

12. The combination of claim 10, wherein the cam follower and cam track function as a slip clutch in the reverse direction of rotation of the spindle.

13. The combination of claim 10, further including an outer ring concentrically about the cam to radially retain the cam follower.

14. The combination of claim 10, wherein the cam follower comprises a ball.

15. The combination of claim 10, wherein the cam track has a helix angle of less than 7 degrees.

16. The combination of any of claims 14 or 15, wherein the cam track terminates on its high side in a flat ledge for positioning the cam follower thereon upon reversal of the spindle rotation.

17. The combination of claim 10, wherein the tool comprises a portable electric tool having a housing with a motor therein for driving the spindle.

18. The combination of claim 17, wherein the portable electric tool comprises a cordless drill.

19. The combination of claim 18, wherein the tool comprises a surgical drill having a cannulated spindle provided with a through bore, and wherein the tool element comprises a K-wire received within the bore of the cannulated spindle.

20. The combination of claim 10, wherein the tool comprises a portable pneumatic tool.

21. The combination of claim 10, wherein the tool comprises a portable hobbyist tool powered by a flexible cable.

22. The combination of claim 10, wherein the tool comprises a manually-operable device.

23. In a surgical drill of the type having a cannulated driving spindle provided with a longitudinal through bore for receiving a K-wire or the like, means for retaining the wire with respect to the spindle for conjoint rotation in unison, said means comprising, in combination, a nose housing enclosing the spindle and having an internally-tapered forward portion and a cylindrical rearward portion, a driven collet having a slotted externally-tapered portion projecting forwardly of the spindle and seated within the complementary internally-tapered forward portion of the nose housing, the collet having an open position and a closed position for retaining the K-wire therein, a shoulder member mounted on the spindle, a cam freely mounted on the spindle rearwardly of the shoulder member, the cam being secured to the rearward cylindrical portion of the nose housing, a stationary thrust ring retained in the housing rearwardly of the cam, the cam having a rearward portion formed with a cam track, a ball between the cam track and the thrust ring, means for retaining the ball radially of the spindle, resilient means between the cam and the shoulder member, constantly urging the cam and hence the nose housing in a direction rearwardly of the spindle, thereby closing the collet and securing the K-wire therein, the ball having a loose engagement in the cam track in one direction of rotation of the spindle corresponding to the driving mode of operation of the tool, and the cam track engaging the ball in the opposite direction of rotation of the spindle to move the cam and hence the nose housing axially along the spindle and forwardly of the drill and against the force of the resilient means, thereby separating the complementary tapered portions of the collet and nose housing, respectively, and thereby opening the collet to facilitate release of the K-wire therefrom.

24. In a power tool having a housing and a spindle journaled therein for rotation in forward and reverse directions, respectively, the tool further having a collet with a tool element retained therein, the subcombination of cam means including a cam member, a cam track formed on the cam member, and a cam follower, the cam follower being disengaged from the cam track in the forward direction of spindle rotation, the cam means thereby functioning as an overrunning clutch in the forward direction, and the cam track engaging the cam follower in the reverse direction of spindle rotation to move the cam member within the housing to open the collet to facilitate removal of the tool element therefrom, the cam means thereby functioning as a slip clutch in the reverse direction of spindle rotation.

25. The subcombination of claim 24, wherein the cam follower comprises a ball, and wherein the cam track has a helix angle of less than 7 degrees.

26. In a power tool having a housing provided with a pistol-grip handle depending therefrom, a motor in the housing, and a spindle journaled in the housing and driven by the motor, the combination of collet means for a tool element driven by the spindle, the collet means having an open position and further having a closed position for securing a tool element therein, an "open" trigger and a "drive" trigger mounted in the pistol-grip handle and projecting forwardly therefrom, the triggers being disposed substantially adjacent to each other and being readily distinguishable from one another by the operator, means responsive to engagement of the "open" trigger for moving the collet means into its open position, thereby to facilitate the insertion of a tool element therein, and means responsive to the subsequent engagement of the "drive" trigger for moving the collet means into its closed position, thereby retaining the tool element therein, the collet being held in its closed position regardless of the continuous engagement of the "drive" trigger, and the collet means being subsequently moved back into its open position only upon the engagement of the "open" trigger, thereby facilitating release of the tool element from the collet means, whereby the operator has immediate and total control without looking at the tool itself and without requiring a shifting of the operator's hand relative to the pistol-grip handle.

27. In a power tool having a housing provided with a pistol-grip handle depending therefrom, a motor in the housing, and a spindle journaled in the housing and driven by the motor, the combination of collet means for a tool element driven by the spindle, the collet means having an open position and further having a closed position for securing a tool element therein, an "open" trigger and a "drive" trigger disposed substantially adjacent to each other, the triggers being mounted in the pistol-grip handle and projecting forwardly therefrom, the "drive" trigger being larger than the "open" trigger and having a forward face formed with an arcuate recess therein, whereby the triggers are readily distinguishable from one another by the operator, means responsive to engagement of the "open" trigger for moving the collet means into its open position, thereby to facilitate the insertion of a tool element therein, and means responsive to the subsequent engagement of the "drive" trigger for moving the collet means into its closed position, thereby retaining the tool element therein.

* * * * *